(12) United States Patent
Jung et al.

(10) Patent No.: US 8,236,368 B2
(45) Date of Patent: Aug. 7, 2012

(54) METHOD FOR PREPARING A HOLLOW MICRONEEDLE

(75) Inventors: Hyung Il Jung, Seoul (KR); Kwang Lee, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 611 days.

(21) Appl. No.: 12/528,117

(22) PCT Filed: Jul. 20, 2007

(86) PCT No.: PCT/KR2007/003507
§ 371 (c)(1),
(2), (4) Date: Aug. 21, 2009

(87) PCT Pub. No.: WO2008/010682
PCT Pub. Date: Jan. 24, 2008

(65) Prior Publication Data
US 2010/0114043 A1    May 6, 2010

(30) Foreign Application Priority Data
Jul. 21, 2006  (KR) .................. 10-2006-0068514

(51) Int. Cl.
*A61L 33/02*  (2006.01)
(52) U.S. Cl. ............... 427/2.24; 427/2.25; 427/250
(58) Field of Classification Search ............ 427/2.24, 427/2.25, 250
See application file for complete search history.

(56) References Cited

U.S. PATENT DOCUMENTS

| 6,334,856 | B1 * | 1/2002 | Allen et al. .................. 604/191 |
| 6,663,820 | B2 * | 12/2003 | Arias et al. .................. 264/496 |
| 2002/0082543 | A1 * | 6/2002 | Park et al. .................. 604/21 |
| 2002/0138049 | A1 * | 9/2002 | Allen et al. .................. 604/272 |
| 2004/0060902 | A1 * | 4/2004 | Evans et al. .................. 216/41 |
| 2004/0186419 | A1 * | 9/2004 | Cho .................. 604/22 |
| 2005/0137531 | A1 * | 6/2005 | Prausnitz et al. .................. 604/173 |
| 2005/0209565 | A1 * | 9/2005 | Yuzhakov et al. .................. 604/173 |
| 2005/0220836 | A1 * | 10/2005 | Falotico et al. .................. 424/423 |
| 2006/0129225 | A1 * | 6/2006 | Kopia et al. .................. 623/1.13 |
| 2006/0206057 | A1 * | 9/2006 | DeRuntz et al. .................. 604/224 |
| 2011/0005669 | A1 * | 1/2011 | Lee et al. .................. 156/256 |

OTHER PUBLICATIONS

Gardeniers, Han J.G.E., et al., "Silicon Micromachined Hollow Microneedles for Transdermal Liquid Transport". Journal of Microlectromechanical Systems, vol. 12, No. 6, Dec. 2003, pp. 855-862.*
McAllister, Devin V., et al., "Microfabricated Microneedles for Gene and Drug Delivery". Annu. Rev. Biomed. Eng. 2000. 02:289-313.*
He, Yuehui, et al., "Novel tungsten oxide microneedles with nanosized tips". Applied Physics Letters 88, 223107 (2006) pp. 1-2.*

* cited by examiner

*Primary Examiner* — Bret Chen
(74) *Attorney, Agent, or Firm* — Clark & Elbing LLP

(57) ABSTRACT

The present invention relates to a method for preparing a hollow microneedle comprising preparing a solid microneedle by drawing lithography; plating the surface with a metal; removing the solid microneedle; and fabricating the hollow microneedle. The present invention ensures efficient preparation of a hollow microneedle with desired hardness, length, and diameter, and which may be effectively used for extracting internal analytical materials from the body and for drug injection.

2 Claims, 7 Drawing Sheets

METHOD FOR PREPARING A HOLLOW MICRONEEDLE

CROSS-REFERENCE TO RELATED APPLICATIONS

This application claims priority under 35 U.S.C. §371 from international application PCT/KR2007/003507, filed Jul. 20, 2007, which claims priority from Korean Patent Application No. 10-2006-0068514, filed Jul. 21, 2006.

TECHNICAL FIELD

The present invention relates to a hollow microneedle and a fabrication method thereof.

BACKGROUND ART

Generally, needles are used in sampling of analytical materials such as blood, for diagnosis of various diseases, or drug injection into the body. With the development of various diagnosing techniques and diagnosing chips, the demand for extracting analytical materials from the body has increased. Under such circumstances, a needle which may cause pain during its use and leave an external mark on the skin has hindered the use of such various diagnosing techniques and devices. As a result, microspikes and solid microneedles which are penetration type needles and hollow microneedles which are open tip type needles have been suggested.

Unlike conventional needles, the microneedles should not cause pain when they penetrate the skin, and for such painless skin penetration, the diameter of the upper end part of the needle is a matter to be considered. The microneedle should have a physical hardness sufficient to penetrate the 10-20 μm of stratum corneum. The microneedles should have a length sufficient to reach the capillary vessel for a high efficient analytical material detection and drug delivery. Since in-plane microneedles were suggested ("Silicon-processed Microneedles", Journal of microelectrochemical systems Vol. 8, No 1, March 1999), various types of microneedles have been developed. For example, a solid silicon microneedle array fabricated using an etching method was suggested as an out-of-plane microneedle array (U.S. Patent Publication No. 2002138049, entitled "Microneedle devices and methods of manufacture and use thereof"). However, since the solid silicon microneedle according to this method was not a hollow structure, it could not be used for analytical material detection in the body and delivery of drugs. As a developed embodiment of an etching technique, a hollow silicon microneedle with an inclination angle was developed by Nanopass Ltd. (W00217985; W02005049107; "Silicon Micromachined Hollow Microneedles for Transdermal Liquid Transport", Journal of microelectrochemical systems, Vol 12, No. 6, December 2003). Hollow silicon microneedles of side-open type and cross type were suggested by Griss and Steme in Stanford University ("Side-Opened Out-of-Plane Microneedles for Microfluidic Transdermal Liquid Transfer", Journal of microelectro-chemical systems, Vol. 12, No. 3, June 2003; U.S. patent application No. US2004267205). As such, various hollow silicon microneedles have been developed, but these caused pain upon penetration of the skin owing to their large diameter, and were not efficient in extracting internal analytical materials from the body and drug delivery owing to their length of 500 μm.

A method for preparing hollow metal microneedles was disclosed by Prausnitz, at the University of Georgia, which comprises fabricating a mold by using a laser and then using deposition and electroplating for preparing the microneedles ("Hollow Metal Microneedles for Insulin Delivery to Diabetic Rats", IEEE Transactions on biomedical engineering, Vol. 52, No. 5, May 2005). However, the hollow metal microneedles prepared by the above method, also had the problem of other conventional methods, with respect to diameter and length. Another method for preparing a novel hollow glass microneedle which has a length of about 900 μm and an inclination angle by extending a glass micropipette, was further suggested by Prausntiz, at the University of Georgia ("Microinfusion Using Hollow Microneedles", Pharmaceutical Research, Vol. 23, No. 1, January 2006, and "Mechanism of fluid infusion during microneedle insertion and retraction", Journal of Controlled Release, 2006, 357361). However, this method also failed to prepare hollow microneedles having a diameter (outer diameter) of 50 μm or less. Further, such hollow microneedle made of glass, i.e. a non-conducting substance, had a limitation in its commercialization due to problems in combining it with a variety of electric devices. Although other various types of hollow microneedles have been suggested by 3M, P&G, BD technologies, Alza Corporation and the like, none of these could provide a means to effectively solve the problems connected with diameter, length and hardness. Accordingly, there still has been a great demand for a hollow microneedle which has a diameter fine enough to achieve painless penetration of the skin, a length which is long enough to penetrate the skin to the deeper area, and suitable hardness.

DISCLOSURE OF INVENTION

Technical Problem

Therefore, it is an object of the present invention to provide hollow microneedles.

Another object of the present invention is to provide a method for fabricating hollow microneedles.

Technical Solution

The present inventors have made a great effort to develop a method for preparing a hollow microneedle, with desired hardness, length and diameter, and finally have succeeded in developing such a hollow microneedle, by preparing a solid type microneedle by drawing lithography; plating the surface with a metal; removing the solid type microneedle; and fabricating the hollow microneedle.

To achieve the above objects of the present invention, the present invention provides a method of using drawing lithography to fabricate biodegradable solid microneedles. According to the present invention, the entire surface of a substance is first coated with a biodegradable viscous material to be formed into microneedles. Alternatively, only the portion of the substrate, on which microneedles are to be formed, that is, the area that is to be brought into contact with pillars formed on a frame in the desired pattern, is selectively coated with the polymer to form a pattern. The coated material is maintained at a suitable temperature, such that it is not solidified. After the pillars formed on the frame in the desired pattern are brought into contact with the surface of the coated viscous material, the coated viscous material is solidified while it is drawn with the frame. As a result, the coated viscous material forms a structure which has a diameter decreasing from the substrate toward the surface contacting with the frame. The drawing process can be carried out by fixing the substrate and moving the frame upward or downward. Alternatively, it can also be performed by fixing the frame and moving the substrate upward or downward. At this time, solid microneedles having a thin and long structure are fabricated either by increasing the drawing speed, such that a force greater than the tensile strength of the coated material is applied to the coated material, or by cutting a specific portion of the coated material using a laser beam. The material being coated over the substrate for forming a solid type microneedle is not specifically restricted, however they should be removable by using a solvent or physical methods, after a metal plating step. The temperature during the formation of a microneedle and the frame drawing rate can be properly adjusted, depending on the characteristics of the coating material, for example viscosity, and the desired structure of the solid type microneedle.

Next, the obtained solid type microneedle is deposited with a suitable material by metal vapor deposition, followed by protecting the upper end part. Then, the deposited surface is plated with metal. Protection of the upper end part may be carried out by applying an enamel or SU-8 to the upper area, without being limited to this. As for the metal, metals which can be applicable to a human body, such as nickel or materials for a needle of a disposable syringe approved by the KFDA (Korea Food & Drug Administration) including stainless steel, aluminum, chrome or the like can be used. The metals should not be toxic or carcinogenic for the human body, but have excellent biocompatibility without the risk of a rejection reaction, good mechanical properties such as tensile strength, elastic modulus, abrasion resistance or the like, and strong corrosion resistance which can endure the corrosive environment in the human body.

For example, cobalt-based alloys, and titanium and alloys thereof could be used as plating materials for a microneedle. In the meantime, the metal microneedle can be coated with a lubricant such as glycerin, for the convenience of penetrating the skin, or with an anticoagulant solution such as citrate or EDTA, in order to prevent blood coagulation during blood collection. After the plating, the solid type microneedle is removed therefrom, resulting in a hollow microneedle. The solid type microneedle can be removed by using a suitable solvent, combustion, or a physical method.

In summary, the method for preparing a hollow microneedle of the present invention comprises the steps of: i) coating the surface of a substrate with a viscous material for forming a solid type microneedle; ii) solidifying the viscous material while drawing the viscous material coating with the frame which has been patterned as a pillar; iii) cutting a certain part of the drawn viscous material coating to form a solid type microneedle; iv) carrying out metal vapor deposition on the surface of the solid type microneedle; v) protecting the upper end part of the solid type microneedle, and then metal-plating the surface of the resulting microneedle; and vi) removing the solid type microneedle by using a suitable solvent or the like.

Another method for preparing a hollow microneedle of the present invention comprises the steps of: i) coating the surface of a substrate with a viscous material for forming a solid type microneedle; ii) solidifying the viscous material while drawing the viscous material coating with the frame which has been patterned as a pillar; iii) cutting a certain part of the drawn viscous material coating to form a solid type microneedle; iv) carrying out metal vapor deposition on the surface of the solid type microneedle; v) metal-plating the surface of the resulting solid type microneedle; vi) cutting the upper end part of the solid type microneedle; and vii) removing the solid type microneedle by using a suitable solvent or the like.

In the present invention, the cutting of a microneedle can be conducted by accelerating the drawing speed in order to apply a force greater than the tensile strength to the coating material, or by using a laser beam, without being limited to these methods.

The hollow microneedle prepared by the present invention can be prepared to have a desired shape, without limitation of the outer diameter (OD), inner diameter (ID) and length. However, for the purpose of extracting internal analytical materials from the body and of drug injection, it is preferred to have an outer diameter of 25-100 μm and an inner diameter of 10-50 μm at the upper end part, and an effective length of 500-2,000 μm.

BEST MODE FOR CARRYING OUT THE INVENTION

Figure 1:
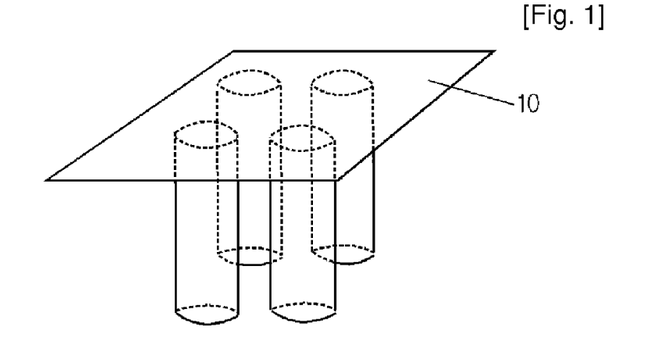
FIG. 1 shows a frame and pillars patterned thereon, which are used for the drawing of microneedles.
Figure 2:
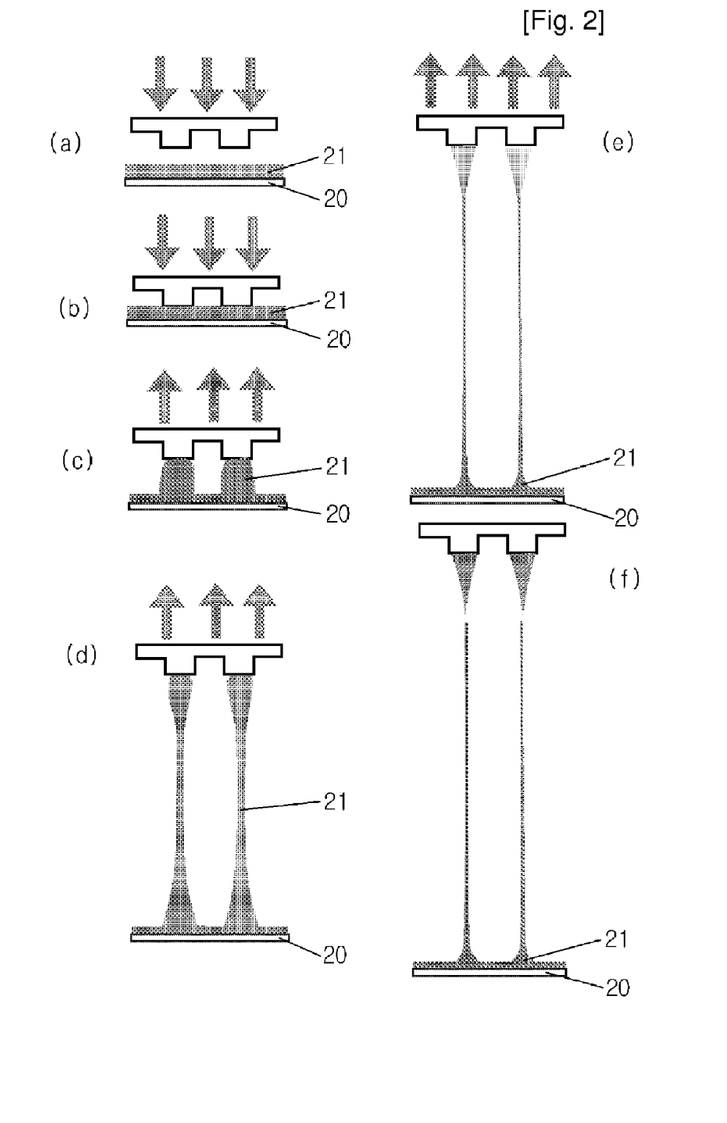
FIGS. 2a to 2f schematically show the process of fabricating solid microneedles according to the present invention.

Hereinafter, the present invention will be described in further detail with reference to the accompanying drawings. FIG. 1 shows a frame 10 and 2×2 pillar patterns 20 formed thereon. Although the diameter of the resulting microneedles depends on the diameter of the pillar patterns formed on the frame, the diameter of the biodegradable solid microneedles may be made smaller than the diameter of the pillars patterned on the frame. Also, when a large number of pillar patterns are formed on the frame, it is possible to produce a large amount of microneedles. The frame is preferably made of one selected from among metals and reinforced plastics, which do not show a great change in their properties upon changes in temperature and humidity, but the scope of the present invention is not limited thereto. The frame used in the fabrication of the microneedles may be reused after washing. FIGS. 2a to 2f are views showing a process of fabricating solid microneedles. As shown in the figures, a parafilm, an aluminum foil or a band is first applied on a substrate 20 having excellent heat conductivity, such as glass or metal, and then a material for forming microneedles is coated on the substrate to form a film 21. The coated material, drawing rate and applied temperature are the main factors to decide the structure of the resulting biodegradable microneedles, and these factors may be suitably adjusted depending on the desired length and diameter.

Figure 3:
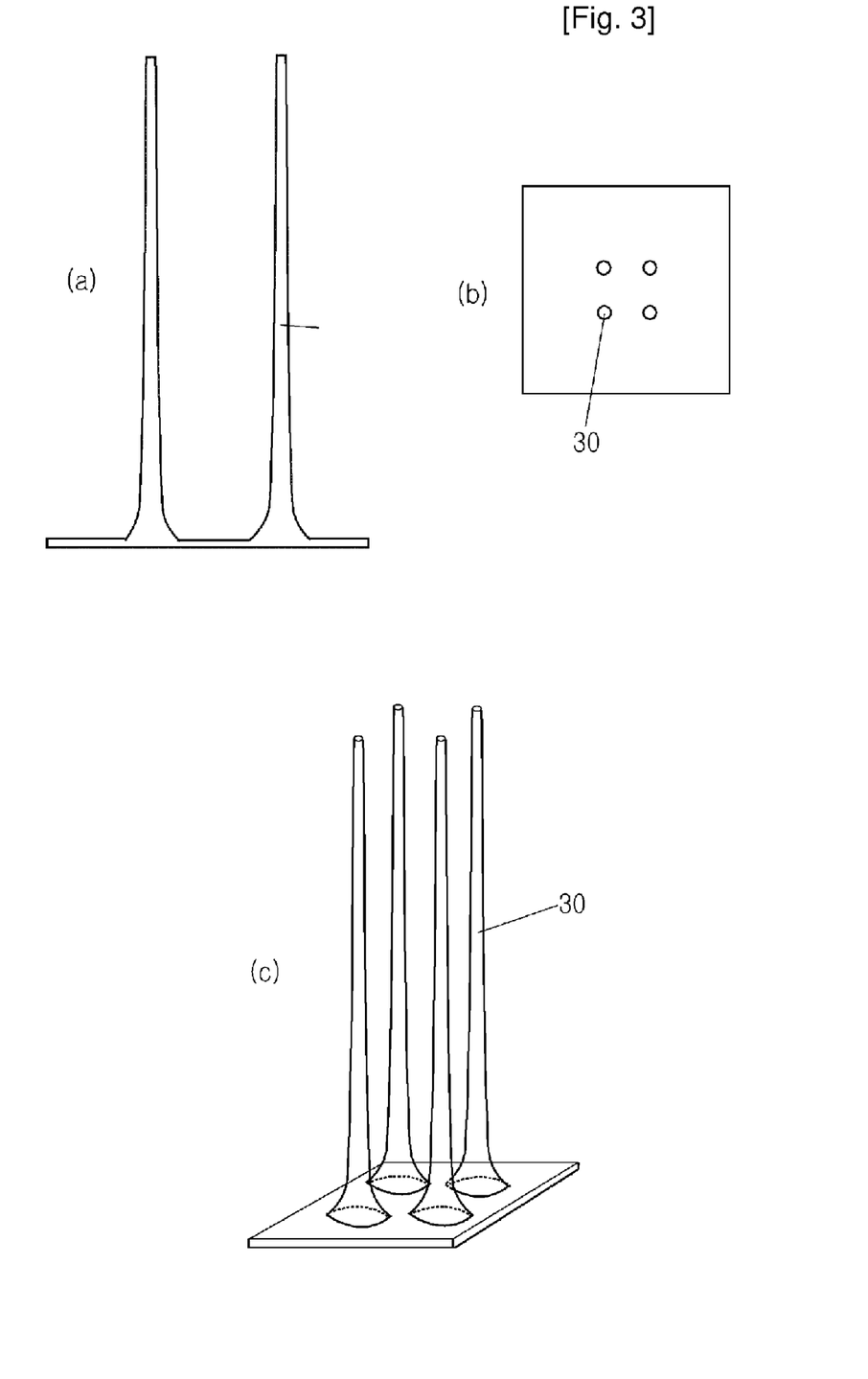
FIGS. 3a to 3c show the structure of solid microneedles according to the present invention.

FIG. 3a is a side view of biodegradable solid microneedles 30 fabricated according to the method of the present invention; FIG. 3b is a plan view of the biodegradable solid microneedles 30; and FIG. 3c is a side view thereof, inclined at an angle of 45°.

Figure 7:
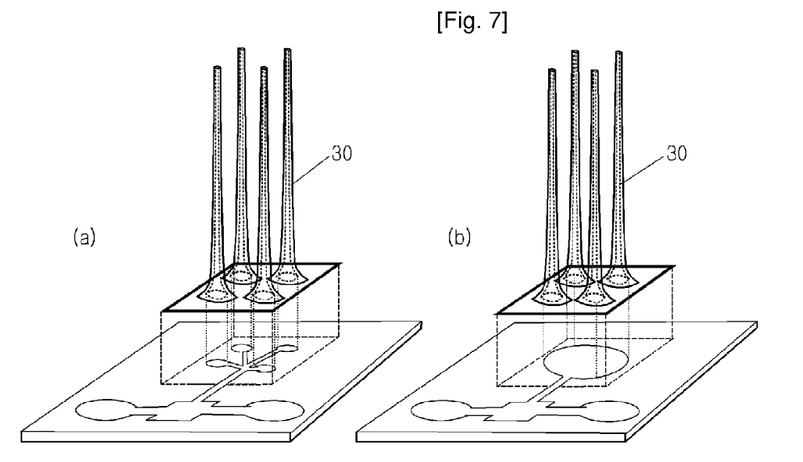
FIGS. 7a and 7b are views showing an example in which a hollow microneedle of the present invention is applied to a microfluidic channel system.
Figure 8:
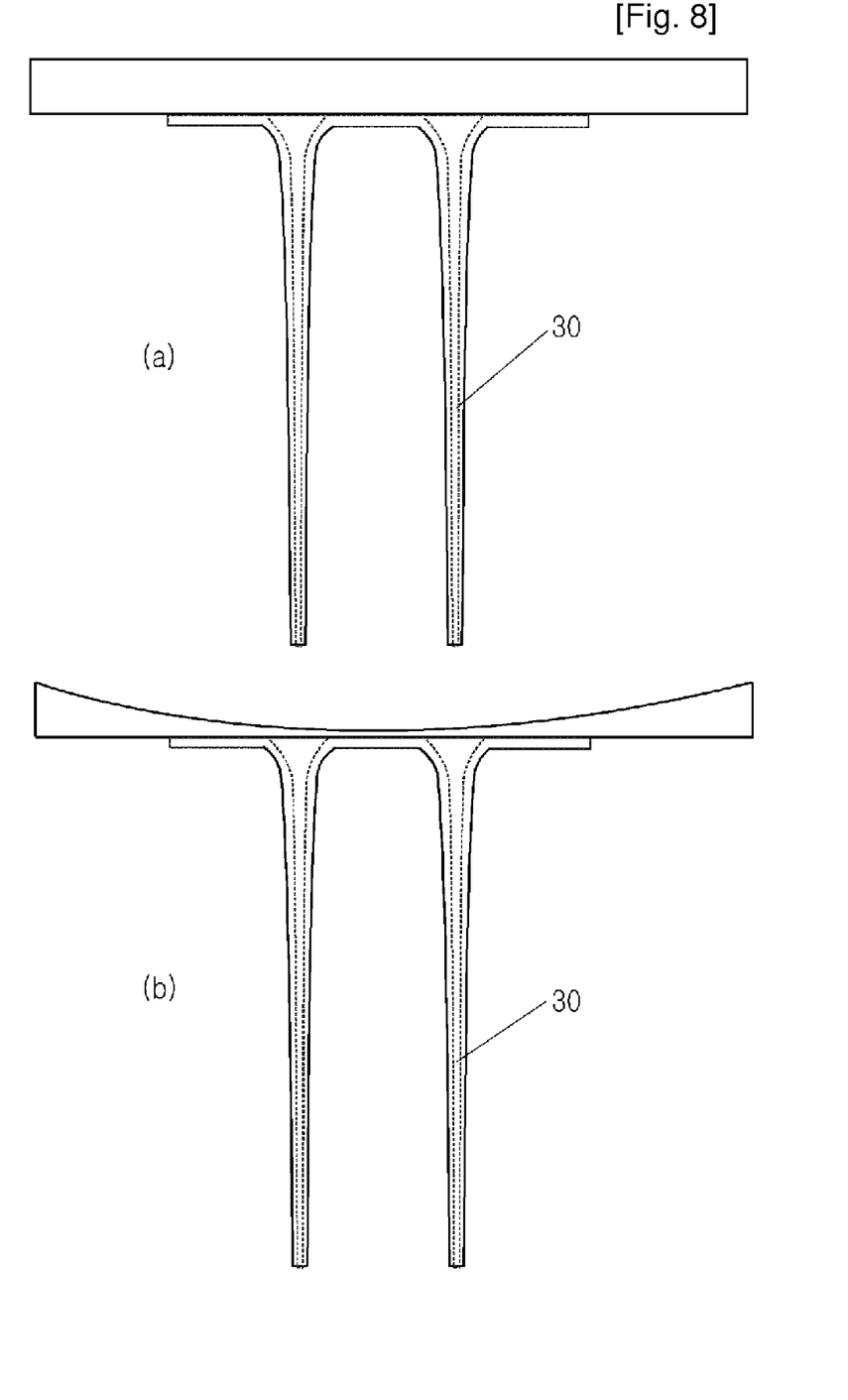
FIGS. 8a to 8b are a view showing an example in which a hollow microneedle of the present invention is applied to a microactuator.
Figure 9:
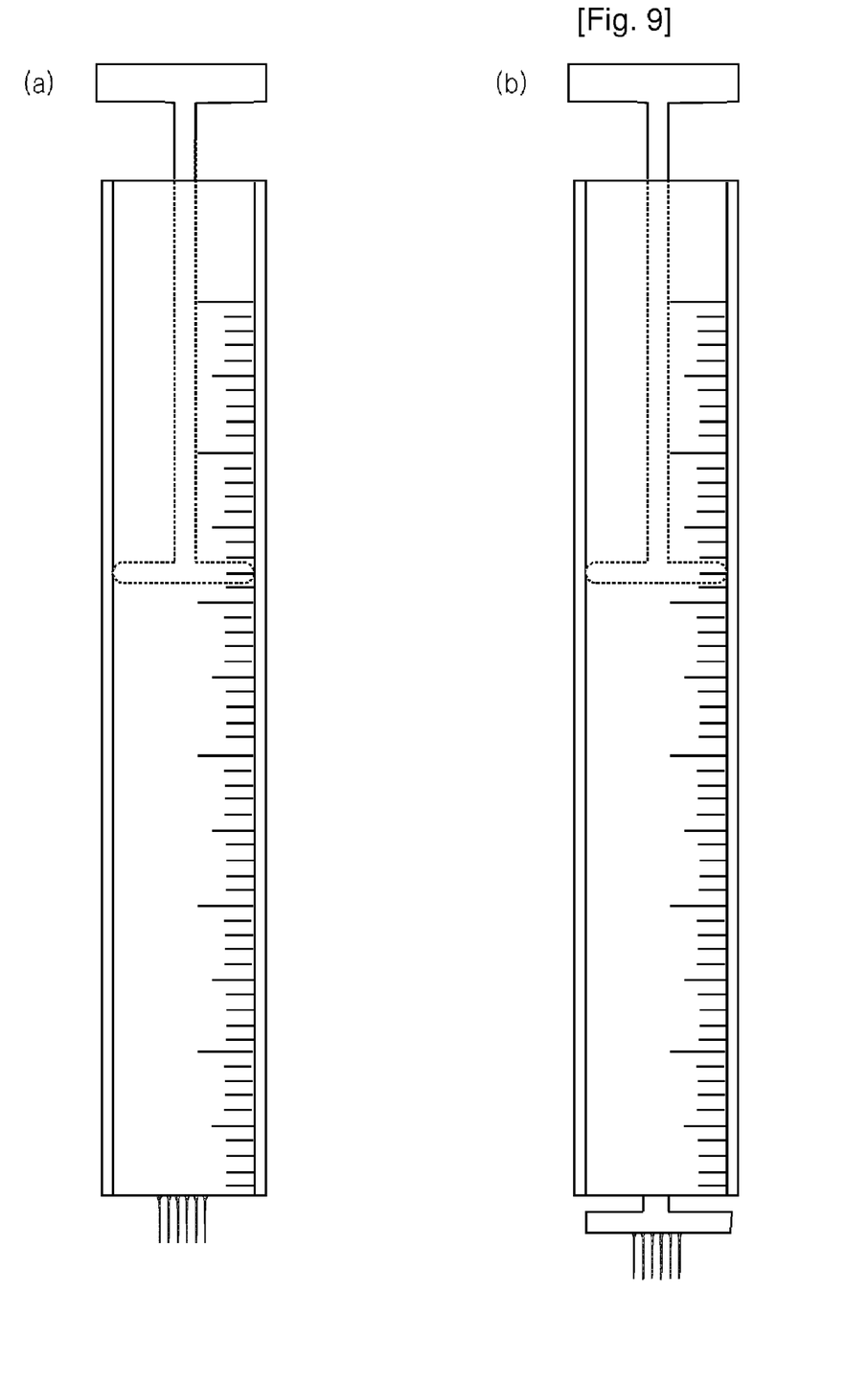
FIGS. 9a to 9b are a view showing an example in which a hollow microneedle of the present invention is applied to a syringe.

FIG. 7 is a view showing a combination of a hollow microneedle (30) with a microfluidic channel system. The lower end part of the hollow metal microneedle is combined with the microfluidic channel system, for extracting internal analytical materials such as blood from the body, and drug delivery. The microfluidic channel system is comprised of a sensor for measuring the analytical materials, a drug injection part and the like. As such, the hollow microneedle of the present invention can be used with various types of microfluidic channel systems by being combined together. FIG. 8 is a view showing an example where a hollow microneedle (30) of the present invention is applied to a microactuator. The microactuator is a device required by portable equipment for extracting analytical materials from the body and for drug delivery. The hollow microneedle of the present invention can be used to extract analytical materials and to deliver drugs, by being combined with the microactuator (See FIG. 8). Similarly, a hollow microneedle of the present invention can be variously used in a piezoelectric pump, Mesotherapy, a roller type and so on. Further, as illustrated in FIG. 9, the hollow microneedle can be applied to a syringe.

As used herein, the term "upper end" of a microneedle means one end of the microneedle, at which the diameter is the minimum.

As used herein, the term "effective length" means the vertical length from the upper end of the microneedle to the position having an inner diameter of 50 μm.

As used herein, the term "solid type microneedle" means a microneedle which is formed in the solid state without hollow holes.

Hereinafter, the present invention will be described in further detail with reference to examples. It is to be understood, however, that these examples are illustrative only, and the scope of the present invention is not limited thereto. Also, it is to be understood that various modifications, variations or changes, which are apparent to one skilled in the art when reading the specification of the present invention, all fall within the scope of the present invention. All the literature cited in the present specification is incorporated herein by reference.

EXAMPLES

Example 1

Preparation of Solid Type Microneedle

SU-8 2050 photoresist (commercially purchased from Microchem) having a viscosity of 14,000 cSt was used to fabricate solid microneedles. For this purpose, SU-8 2050 was coated on a flat glass panel to a certain thickness, and it was maintained at 120° C. for 5 minutes to maintain its flowing properties. Then, the coated material was brought into contact with a frame having 2×2 pillar patterns formed thereon, each pillar having a diameter of 200 μm (See FIG. 1). The temperature of the glass panel was slowly lowered to 95-90° C. over about 5 minutes to solidify the coated SU-8 2050 and to increase the adhesion between the frame and the SU-8 2050. Then, while the temperature was slowly lowered from 95-90° C., the coated SU-8 2050 was drawn at the speed of 1 μm/s for 60 minutes using the frame which adhered to the coated SU-8 2050 (See FIG. 2). After 60 minutes of drawing, solid microneedles, each having a length of about 3,600 μm, were formed. Subsequently, the solid microneedles were cured for 30 minutes, and then the drawing speed was increased to 700 μmm/s in order to separate the microneedles from the frame, thus fabricating microneedles, each having a length of more than 2,000 μm. Alternatively, the formed microneedles could be separated from the frame by cutting. As a result, microneedles, each having an upper end diameter of 10-40 μm, an effective length of 2,000 μm and a total length of 3,000 μm, were fabricated.

Example 2

Preparation of Hollow Microneedle

Figure 4:
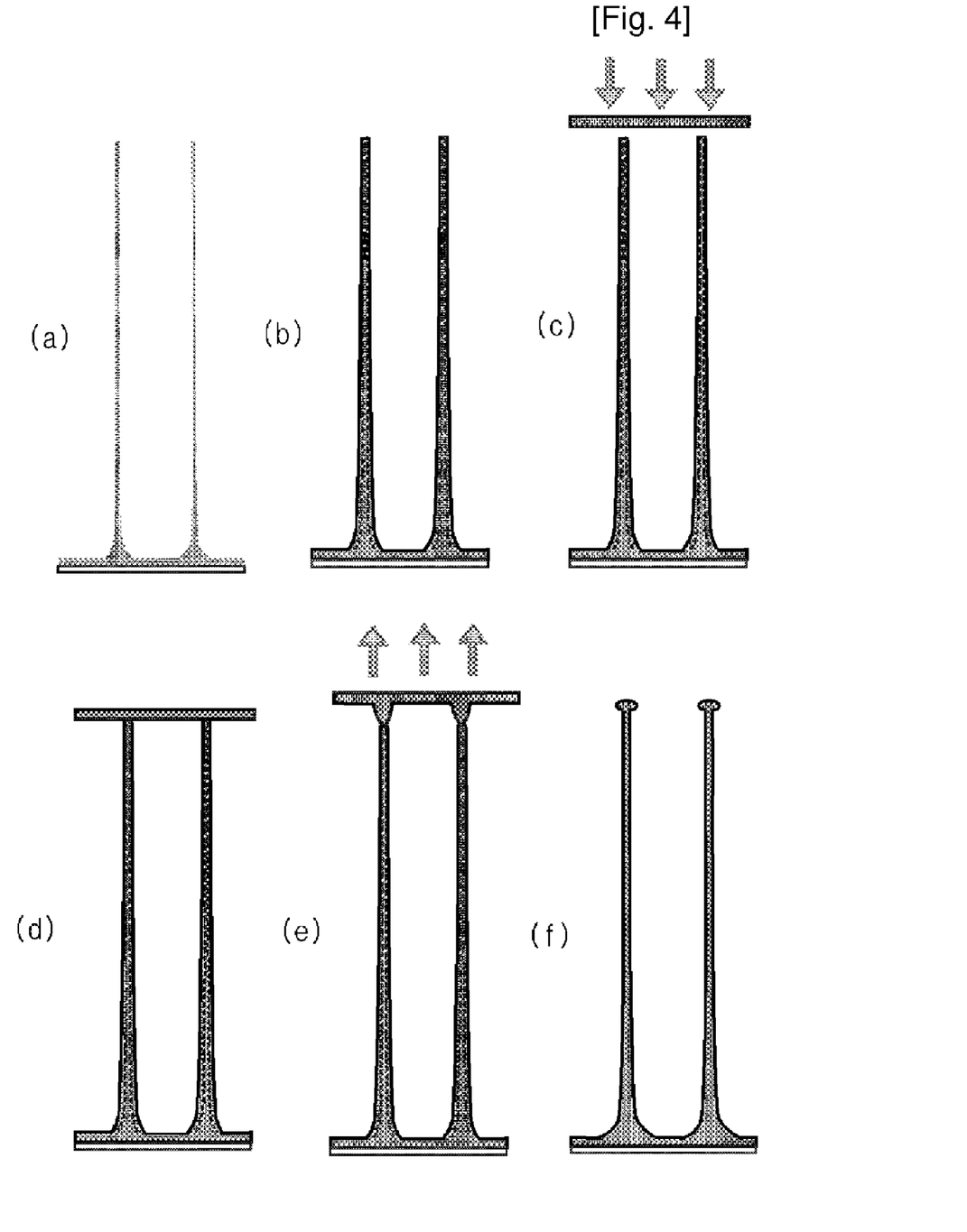
FIGS. 4a to 4f are a schematic view showing the metal vapor deposition on a solid type microneedle and its protection.

Three layers of Ti-Cu-Ti (100 μm-300 μm-100 μm) were deposited on the SU-8 solid type microneedle (30) (FIG. 4a) prepared from Example 2 by sputtering (FIG. 4b).

Figure 5:
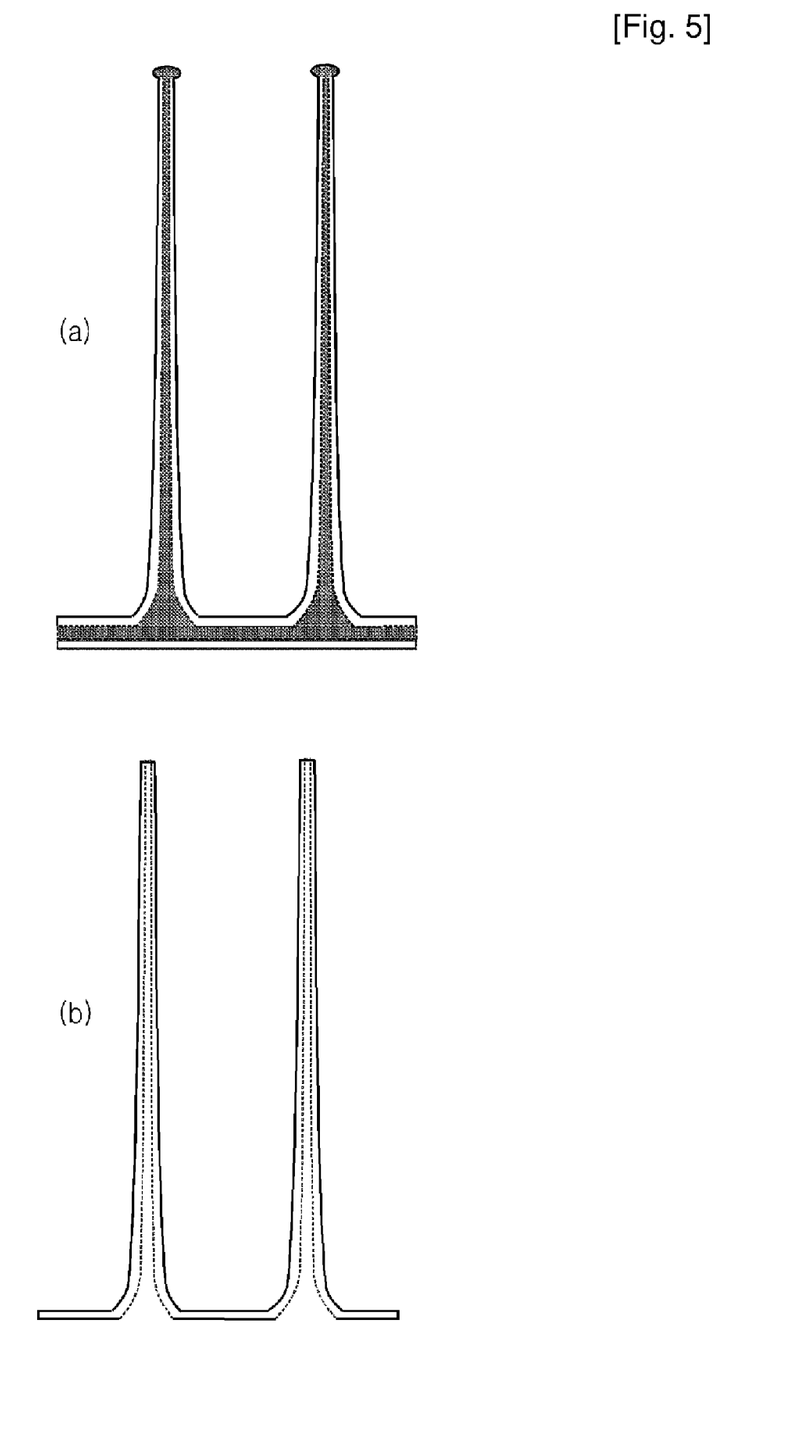
FIGS. 5a to 5b are a schematic view showing the preparation process of a hollow microneedle in which a solid type microneedle deposited with metal is metal-plated and then the solid type microneedle is removed therefrom.
Figure 6:
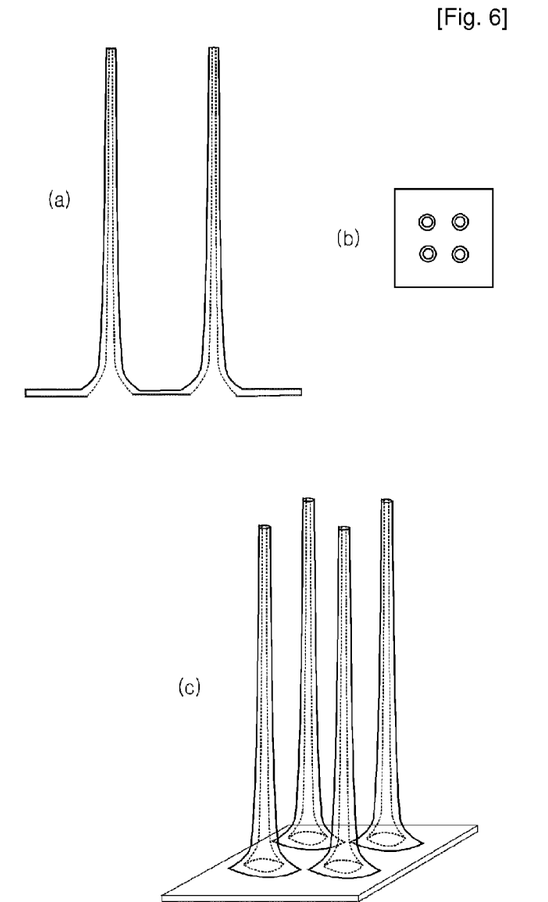
FIGS. 6a to 6c are views showing the structure of a hollow microneedle prepared according to the present invention.

As another example, an Ag layer was deposited on the SU-8 solid type microneedle (30) (FIG. 4a), when a sliver mirror reaction was used (FIG. 4b). Next, the upper end part of the deposited solid type microneedle was protected with enamel or SU-8 2050 (See, FIGS. 4c to 4f). The enamel or SU-8 2050 treatment to the upper end part is to prevent the upper end part from being metal-plated in the subsequent step. Then, the surface of the solid type microneedle, the upper end part of which was protected, was electroplated with nickel (FIG. 5a). The Ni electroplating was carried out at 0.206 μm/min. per 1 A/d for 60 minutes, resulting in a plated metal thickness of 10 μm and an outer diameter of 50 μm. The plating metal thickness was controlled depending on the plating time. As another example, the electroplating was carried out for 3 hours, resulting in a plated metal thickness of 35 μm and outer diameter of 100 μm. The plated structure was placed into boiling water at a temperature in the range of 90-100° C. for 30 minutes so as to conduct the primary removal of SU-8 2050 from the solid type microneedle and enamel simultaneously. The resulting structure was again placed into an SU-8 remover (commercially purchased from Microchem) or acetone for about 1 hour to secondly remove the solid type microneedle made of SU-8 2050 and sealed enamel (FIG. 5b). FIG. 6a is a side view of the completed hollow metal microneedle. It was found that the prepared hollow metal microneedle had an outer diameter (OD) of 25-100 μm; an inner diameter (ID) of 10-50 μm; an effective length of 1,500 μm ; and a total length of 3,000 μm. FIG. 6b is a plan view of a hollow metal microneedle, when viewed from above, and FIG. 6 c is a slanted view thereof at 45°.

As described above, according to the present invention, it is possible to prepare a hollow microneedle with the targeted diameter, length and hardness. Therefore, the hollow microneedle according to the present invention can be useful for combining with devices for taking analytical materials such as blood from the body, and for injecting drugs.

The invention claimed is:

1. A method for preparing a hollow microneedle, which comprises the steps of: i) coating a surface of a substrate with a viscous material for forming a solid microneedle; ii) contacting the viscous material with a frame which has been patterned as a pillar; iii) solidifying the viscous material while drawing the viscous material with the frame; iv) cutting a certain part of the drawn viscous material coating to form a solid microneedle; v) carrying out metal vapor deposition on a surface of the solid microneedle; vi) protecting an upper end part of the solid microneedle, and then metal-plating the surface of the resulting microneedle; and vii) removing the solid microneedle by using a suitable solvent.

2. A method for preparing a hollow microneedle, which comprises the steps of: i) coating a surface of a substrate with a viscous material for forming a solid microneedle; ii) contacting the viscous material with a frame which has been patterned as a pillar; iii) solidifying the viscous material while drawing the viscous material with the frame; iv) cutting a certain part of the drawn viscous material coating to form a solid microneedle; v) carrying out metal vapor deposition on a surface of the solid microneedle; vi) metal-plating the surface of the resulting solid microneedle; vii) cutting an upper end part of the solid microneedle; and viii) removing the solid microneedle by using a suitable solvent.

* * * * *